United States Patent [19]

Okano et al.

[11] Patent Number: 5,607,646

[45] Date of Patent: *Mar. 4, 1997

[54] DEVICE FOR SEPARATING POLYNUCLEOTIDES HAVING A PLURALITY OF ELECTRODE-CONTAINING CELLS AND MOVABLE COLLECTING CAPILLARY

[75] Inventors: Kazunori Okano, Shiki; Hideki Kambara, Hachiouji, both of Japan

[73] Assignee: Hitachi, Ltd., Tokyo, Japan

[ * ] Notice: The term of this patent shall not extend beyond the expiration date of Pat. No. 5,434,049.

[21] Appl. No.: 410,544

[22] Filed: Mar. 21, 1995

Related U.S. Application Data

[63] Continuation of Ser. No. 21,667, Feb. 24, 1993, Pat. No. 5,434,049.

[30] Foreign Application Priority Data

Feb. 28, 1992 [JP] Japan .................................. 4-042829

[51] Int. Cl.$^6$ ...................... B01L 11/00; C12Q 1/68
[52] U.S. Cl. .................. 422/101; 422/68.1; 422/82.01; 422/100; 422/104; 435/6
[58] Field of Search ................... 435/6, 287, 291, 435/810; 436/94, 72; 536/25.4; 422/68.1, 82.01, 100, 101, 104

[56] References Cited

U.S. PATENT DOCUMENTS

| | | | |
|---|---|---|---|
| 4,859,302 | 8/1989 | Alfenito | 204/182.8 |
| 4,945,045 | 7/1990 | Forrest et al. | 435/25 |
| 5,089,387 | 2/1992 | Tsay et al. | 435/6 |
| 5,217,591 | 6/1993 | Gombocz et al. | 204/299 R |

FOREIGN PATENT DOCUMENTS 8806189  8/1988  WIPO.

*Primary Examiner*—Kenneth R. Horlick
*Attorney, Agent, or Firm*—Antonelli, Terry, Stout & Kraus, LLP

[57] ABSTRACT

A method for simultaneously detecting a plurality of target polynucleotides in a sample on a single reaction chip and a method for separating a plurality of target polynucleotides are provided. On the reaction chip are arranged a plurality of independent cells for capturing different target polynucleotides. Different probes are immobilized onto the individual cells, and detect the cells where the target polynucleotides are captured, thereby analyzing the species of the captured target polynucleotides. Also, the individual cells function as electrodes to elute the captured target polynucleotides therethrough, thereby separating a plurality of the target polynucleotides.

5 Claims, 3 Drawing Sheets

DEVICE FOR SEPARATING POLYNUCLEOTIDES HAVING A PLURALITY OF ELECTRODE-CONTAINING CELLS AND MOVABLE COLLECTING CAPILLARY

This application is a continuation application of application Ser. No. 08/021,667, filed Feb. 24, 1993, now U.S. Pat. No. 5,434,049.

BACKGROUND OF THE INVENTION

The objective of the present invention relates to a diagnostic method for detecting the presence or absence of exogenous polynucleotides from viruses, rickettsias, bacteria and the like as the etiology of diseases or a polynucleotide carrying specific genetic information in organisms; a polynucleotide preparative method for polynucleotide structural analysis; and an immobilized probe chip used therefor.

Japanese Patent Laid-open No. 58-31998 discloses a method for capturing a target polynucleotide (DNA or RNA) sample on a solid phase as well as a method for detecting a target exogenous polynucleotide from bacteria, viruses and the like in blood and excretion samples. According to such methods, the polynucleotide in a sample is denatured by heating and the like into single strands, which is then immobilized on nitrocellulose membrane. After reacting the membrane with a polynucleotide probe being labeled with a radioisotope and having a nucleotide sequence complementary to the sequence of the polynucleotide of a detecting bacterium or a virus, the membrane is washed. If the polynucleotide of a bacterium or a virus is contained in the sample, the labeled polynucleotide probe hybridizes with the polynucleotide, and thus remains on the membrane. Detection of the associated product by autoradiography enables the determination as to whether or not the target polynucleotide is present.

S. R. Rasmussen et al. describe another method for capturing a target polynucleotide (DNA or RNA) sample on a solid phase in Analytical Biochemistry 198, 128–142(1991). According to the method, the phosphate group at the 5' terminus of a polynucleotide is activated by using 1-methylimidazole and 1-ethyl-3-(3-dimethylaminopropyl)carbodiimide. Then, the polynucleotide is immobilized onto a polystyrene microplate having a secondary amine on the surface thereof. According to the method, the activated 5' terminal phosphate group reacts with the secondary amine, so that the 5' terminal of the polynucleotide is covalently immobilized onto the microplate surface. In this example, a target oligonucleotide in a sample can be captured by using an immobilized polynucleotide. A specific oligonucleotide can be detected using a $^{32}$P-labeled probe according to any of the methods.

SUMMARY OF THE INVENTION

According to the polynucleotide immobilization method described above, the labeled probe to be used for detection should be modified, depending on the subject. Therefore, the measurement of a plurality of subjects should require a number reaction supports corresponding to the number of measuring subjects. It is possible to simultaneously measure several types of measuring subjects, using different fluorophores emitting of different wave lengths as the substances for labeling individual probes. However, increasing the number of measuring subjects causes difficulty in such simultaneous detection.

For the purpose of separating a captured target polynucleotide, the elution of the target polynucleotide alone is difficult because a great number of different polynucleotides are immobilized on a membrane. Furthermore, the polynucleotides are strongly immobilized according to the first conventional method. According to the method of S. R. Rasmussen et al., a support for immobilizing a polynucleotide is used as a probe for hybridizing and capturing a target polynucleotide, so that it may be easy to elute the target polynucleotide. According to the method, however, it is a polynucleotide of a specific sequence to be hybridized with the immobilized probe. Therefore, it is difficult to simultaneously separate a plurality of target oligonucleotides from a supporting well. It is needless to say that a plurality of target polynucleotides can be obtained by a method comprising modifying eluting conditions under ambiguous hybridization conditions. According to such method, however, the separation should be done under unstable conditions, resulting in unsatisfactory separation potency in some cases and ready exposure to the influence of sample state, which frequently causes complex conditioning. Also, it is difficult to separate target oligonucleotides of totally different sequences from each other.

It is an objective of the present invention to provide a polynucleotide capturing chip capable of simultaneously capturing a plurality of target polynucleotides, to provide a method for detecting a plurality of polynucleotides using the same and to provide a method for separating a plurality of target polynucleotides.

In the polynucleotide capturing chip with immobilized probes complementary to target polynucleotides in accordance with the present invention, individually different probes for a plurality of target polynucleotides are independently immobilized on cells formed on different regions on a single chip.

In the method for detecting polynucleotides comprising a process of capturing target polynucleotides attached with a labeling substance onto a polynucleotide capturing support with immobilized probes complementary for the target polynucleotides or comprising a process of capturing target polynucleotides and a process of bonding a labeling substance, a plurality of target polynucleotides are measured using the aforementioned polynucleotide capturing chip as the polynucleotide capturing support.

According to the target polynucleotide separation method comprising capturing target polynucleotides with a polynucleotide capturing support having immobilized probes complementary to the target polynucleotides and then separating the target polynucleotides, each cell of the polynucleotide capturing chip to be used as the polynucleotide capturing support also functions as an electrode for eluting the target polynucleotides, wherein the electric fields applied to such electrodes each with a plurality of immobilized probes can be switched over one by one to elute and separate a plurality of the target polynucleotides.

Figure 1:
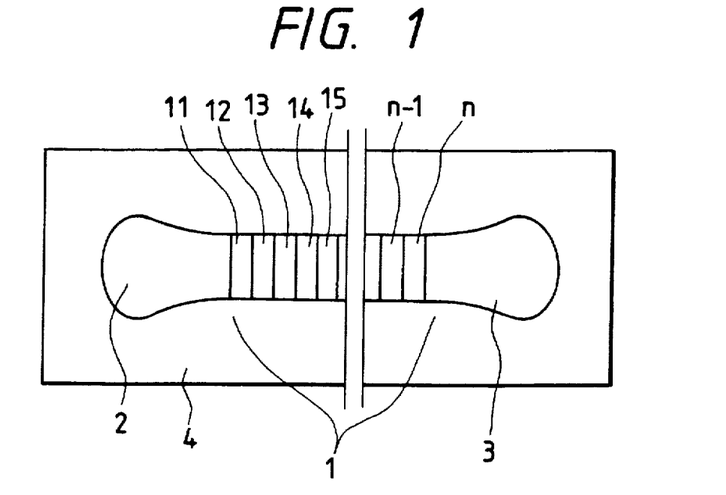
FIG. 1 is a plan view schematically depicting the reaction chip as one embodiment of the present invention.

The present invention for the purpose of simultaneously analyzing and separating a plurality of target polynucleotides is firstly characterized in that a plurality of independent regions for capturing different target polynucleotides which one particular interest are arranged on a single reaction chip, FIG. 1 depicts the general view of the reaction chip in accordance with the present invention, wherein reaction part 1 is composed of a plurality of cells, 11 to n, and individually different polynucleotide probes are immobilized in the individual cells. After the addition of a sample solution under hybridization conditions, the target polynucleotides contained in the sample are captured by hybridization onto the reaction chip. Then, the individual target polynucleotides are captured onto different cells with the immobilized individual polynucleotide probes in accordance with the present invention. For the simultaneous analysis of the target polynucleotides, the labeled substances captured onto the individual cells can be measured using the labeled probes.

For the separation of the target polynucleotides, the target polynucleotides captured onto the individual cells are sequentially eluted. Herein, a problem occurs in that because the individual cells are adjacent to each other, the target polynucleotides captured onto the individual cells may be contaminated with each other.

Figure 6:
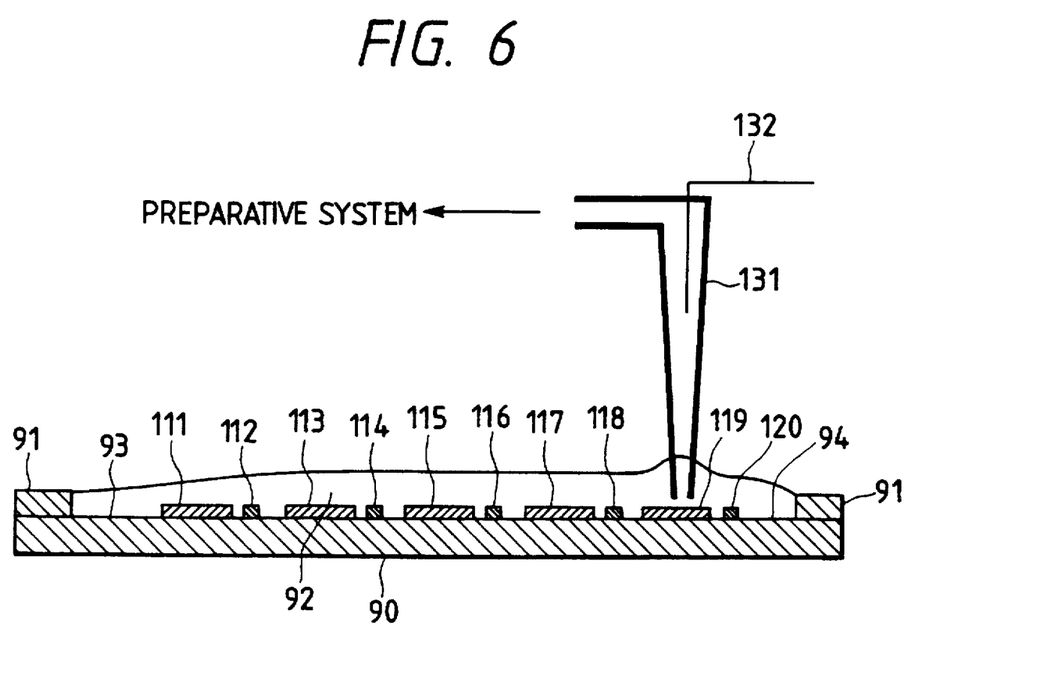
FIG. 6 is a cross sectional view depicting the general constitution of the recovery and separation method of target polynucleotides in accordance with the present invention.

Secondly, the present invention is characterized in the method for eluting target polynucleotides. The target polynucleotides captured onto the chip via a hybridization reaction are readily eluted via heating and the like. The present invention is constituted, as is shown in FIG. 6, such that an electric field can be applied sequentially to individual cells so as to elute a target polynucleotide captured onto each of the cells. In a cell applied with a positive electric field, the addition of a heated eluent cannot trigger the elution by Joule's heat of the target polynucleotide because of the negative charge thereof. If the electric field applied to the cell is switched to negative, the target polynucleotide is eluted via electrostatic repulsion. The sequential switch-over of the electric field regarding all the cells one by one enables the elution and recovery individually of different target polynucleotides captured onto a plurality of the cells without contamination. It should be required to set up a means for immediately recovering eluted target polynucleotides and for preventing the recapturing of the once eluted target polynucleotide onto other cells. This can be accomplished by placing, in a cell intended for separation, a capillary tube with a positive electrode and recapturing the eluted target polynucleotides into the tube.

When a polynucleotide probe capable of complementary bonding to a target polynucleotide reacts with the target polynucleotide under hybridization conditions, a hybrid between the two types of the polynucleotides, namely the target polynucleotide and the probe, is formed. If the polynucleotide probe is immobilized onto a chip, the target polynucleotide should be captured onto the chip. In accordance with the present invention, it is required to arrange a plurality of cells on a chip. Therefore, such chip is preferably a glass or silicon wafer having a plane surface or optically plane plastics. Cells can be readily formed silicon wafer using a photoresist used in the semiconductor process as shown in the following examples. Therefore, a silicon wafer is particularly useful. To immobilize different probes for a plurality of target polynucleotides, it is required to separately activate each of the cells and to immobilize the probes. By sequentially exposing the individual cells using positive-type photoresists, then removing the resists to activate the surfaces, different probes can be immobilized onto appropriate cells.

For the detection of the target polynucleotide captured onto each of the cells, a second probe labeled with fluorophore and the like may successfully be used. The target polynucleotide is bonded, in a sandwich manner, in between the capturing probe immobilized onto each of the cells and the labeled probe, so that each of the cells immobilizes the labeled probe at an amount corresponding to the amount of the target polynucleotide. Thus, the measurement of the intensity of fluorescence gives the information of the amount of the captured target polynucleotide.

For the separation of the target polynucleotide captured onto each of the cells, the increase in temperature causes the separation of the target polynucleotide from the probe. The addition of a high concentration of a quarternary ammonium salt such as tetraethylammonium chloride can set the elution temperature of the target polynucleotide at a nearly constant temperature. Thus, it is possible to recover the captured target polynucleotide if heating is effected at a predetermined temperature. As has been described above, a plurality of target polynucleotides can be recovered without contamination, by switching the electric field applied to a cell one by one on the reaction chip.

DESCRIPTION OF THE PREFERRED EMBODIMENTS

The present invention will now be explained by the examples.

The polynucleotides to be used in the present examples are as follows:

polynucleotide having a nucleotide sequence, Sequence No. 1; Probe No. 1;

polynucleotide having a nucleotide sequence, Sequence No. 2; Probe No. 2;

polynucleotide having a nucleotide sequence, Sequence No. 3; Probe No. 3;

polynucleotide having a nucleotide sequence, Sequence No. 4; Probe No. 4;

polynucleotide having a nucleotide sequence, Sequence No. 5; Probe No. 5;

polynucleotide having a nucleotide sequence, Sequence No. 6; Probe No. 6.

In the present Example, an explanation will follow regarding a method for preparing a reaction chip having a plurality of independent cells with immobilized different polynucleotide probes within the single reaction chip; and a method for detecting target polynucleotides using the same.

EXAMPLE 1

The polynucleotides of Sequence Nos. 1 and 2 are the probes for capturing λ-phage DNA as the target polynucleotide; the polynucleotides of Sequences Nos. 3 and 4 are the probes for capturing M13 phage also as the target polynucleotide. The probes are used after the immobilization onto a reaction chip comprising a silicon wafer, as shown in FIG. 1. The reaction chip comprises reaction part 1 with individually immobilized probes, addition part 2 of samples, labeled probes and the like, and a reaction residual solution discharge part 3, and is of a structure where a solution is retained with preferential bank 4 composed of fluorinated ethylene resin. The reaction part 1 comprises cells 11, 12, 13, 14, - - - n–1, n, capable of immobilizing different probes, and in a first example of the chip of the present Example, probes 1, 2, 3 and 4 are immobilized onto the cells 11, 12, 13 and 14, respectively. The reaction part can be arranged two-dimensionally if the arrangement thereof in one row is not enough, so that the number of different types of probes capable of immobilization can optionally be increased. The immobilization of each probe onto the reaction part 1 of the reaction chip is carried out by the following procedures.

Firstly, the surface of the silicon wafer is vapor oxidized, followed by formation of fluorinated ethylene resin bank 4. The vapor oxidation herein is inevitable of the next process for coating the surface with an aminosilane film, but it is not required to form such a thick oxidized layer as required for the formation of an insulation film during routine semiconductor processes. Then, 3-(2-aminoethylaminopropyl)trimethoxy silane is used to coat the surface of the oxidized film with an aminosilane film to introduce the amino group onto the surface of the silicon wafer. The amino group is then trifluoroacetylated for protection.

Subsequently, a quinone diazide added phenolnovolak resist of a positive type is coated on the surface, which is then baked at 95° C. Because the exposed portions of the resist can be removed in alkaline washing, the repetition of the processes, namely exposure, alkaline washing, removal of trifluoroacetyl group and immobilization of a polynucleotide probe, enables sequential immobilization of individually different probes onto different regions on the silicon wafer. Firstly, the part 11 of the silicon wafer surface is exposed to the light of 350 nm to 400 nm, thereby removing the resist on cell 11. Subsequently, washing is effected in an aqueous trimethylammonium solution, to remove the decomposed resist. Concurrently, the amino group protecting trifluoroacetyl group is also removed. According to the method of S. R. Rasmussen et al. described in Analytical Biochemistry, Vol. 198, 128–142(1991), a first probe having a phosphate group at the 5' terminus is immobilized. That is, the first probe is subjected to reaction in the presence of 1-methyl imidazole buffer, pH 7.0 and 0.2M 1-ethyl-3-(3-dimethylaminopropyl)carbodiimide at 50° C. for 5 hours.

The same procedures are repeatedly carried out for the cells 12, 13 and 14, to immobilize second, third and fourth probes, respectively. Finally, all of the cells are washed in an aqueous trimethylammonium solution to remove the byproducts via carbodiimide. Produced during the above described procedures is a reaction chip having a plurality of independent cells with different immobilized polynucleotide probes on the surfaces thereof.

The method for detecting λ-phage DNA and M13 phage DNA as the target polynucleotides will now be shown below. A fifth probe is a probe for detecting λ-phage DNA and having the 5' terminus labeled with sulforhodamine 101. A sixth probe is a probe for detecting M13 phage and having the 5' terminus labeled with sulforhodamine 101. The method for labeling the 5' termini with sulforhodamine 101 will now be explained in detail. The synthesis of each of the probes is done by the phosphoramidite method. At the final step of the synthesis, the reaction with N-monomethoxytritylaminohexa-6-oxy-β-cyanoethyl-N,N-diisopropylaminophosphoramidite is carried out to introduce the amino group into the 5' termini. After the reaction with 100- - - fold molar sulforhodamine 101 acid chloride in 0.1 M carbonate buffer (pH 9.0), ethanol precipitation followed by electrophoresis involving 7M urea is done to purify the sulforhodamine 101 labeled probes. Thus, the labeled probes are purified products each of a single band by electrophoresis.

In the reaction chip having a plurality of independent cells with the different polynucleotide probes immobilized on the surface thereof are added a mixture solution of λ-phage DNA and M13 phage DNA and a mixture solution of the labeled probes. The reaction chip is heated at 95° C. for 2 minutes, followed by immediate cooling to 0° C. Subsequently, hybridization reaction is effected at 48° C. Washing is done in a buffer containing 0.1% sodium dodecylsulfate at 25° C. for 30 minutes and further washing is then done at 58° C. in a solution of 0.1% sodium dodecylsulfate, 2 mM EDTA, 3M tetramethylammonium, Tris-HCl, pH 8.0. Subsequently, washing is done in 0.05% polyoxyethylene sorbitan monolaurate, 5 mg/ml bovine serum albumin, 0.15 mol/l NaCl and 0.05 mol/l phosphate buffer, pH 7.4. During the procedure, the target polynucleotides can be captured on the reaction chip and labeled with the labeled probes.

Figure 2:
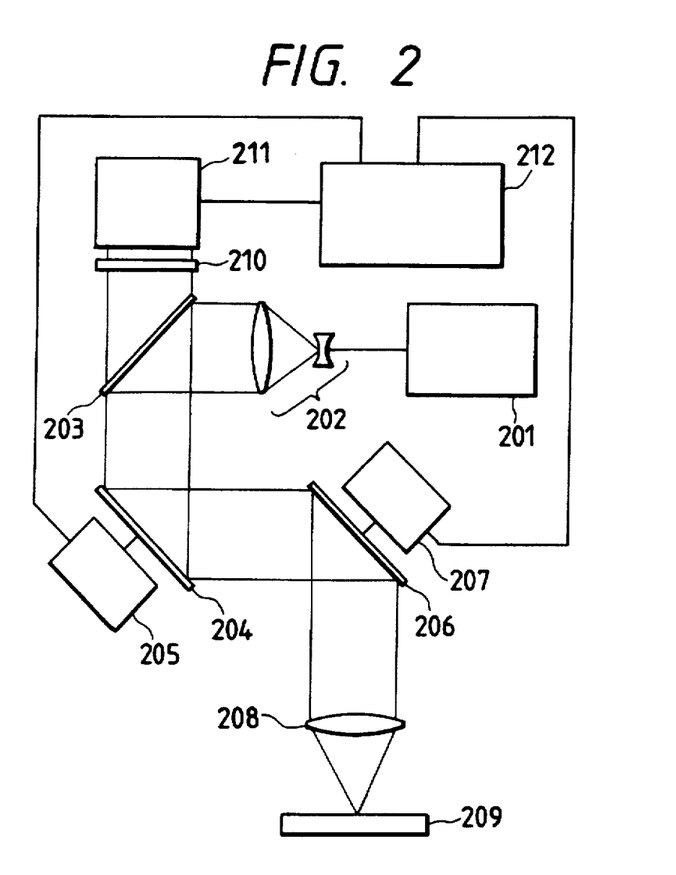
FIG. 2 is a general view depicting the fluorescence measuring device of the present invention.

So as to detect the part of the fluorescent dye-labeled probes bonded to the reaction chip after the termination of the reaction, the fluorescence emitted from the reaction chip is measured, using He/Ne laser at 594 nm (or a Na lamp) and a photomultiplier (or a high-sensitivity line sensor and area sensor). Another optical source and fluorophores may satisfactorily be used in combination. Because a silicon wafer is used as a chip in the present Example, a reflection-type fluorescence measuring device as shown in FIG. 2 is used. The fluorescence measuring device for practical use according to the present invention will now be explained. The light of laser source 201 expands the beam size through beam expander 202, which is then reflected on dichroic mirror 203. As the dichroic mirror 203, there is used the one which can reflect the light of 594 nm and transmits the light of 610 nm or more at a rate of 80% or more. The light reflected on the dichroic mirror 203 is reflected on mirror 204 which angle can be changed with servo motor 205, and is then reflected again on mirror 206 which angle can be changed into the direction orthogonal to the mirror 204. Subsequently, the light is collimated with a condensing lens 208 to irradiate a specific region on the reaction chip 209. Then, the angle between the mirrors 204 and 206 is modified into the direction orthogonal to each other, so that scanning can be done in the X-Y direction on the reaction chip. When the laser spot directly hits a cell with a fluorophore present, fluorescence is emitted from the portion. Fluorescence progresses through condensing lens 208, mirror 206 and mirror 204 in this order and passes through dichroic mirror 203. After passing through bandpass filter 201, fluorescence is detected with photomultiplier 211. The detected signal is incorporated into microprocessor 212, followed by processing thereof while under the synchronization with the angle information from servo motors 205 and 207, thereby calculating the fluorescence intensity at each cell on the reaction chip surface. By the method, the fluorescence intensity per each cell can be measured.

Figure 3:
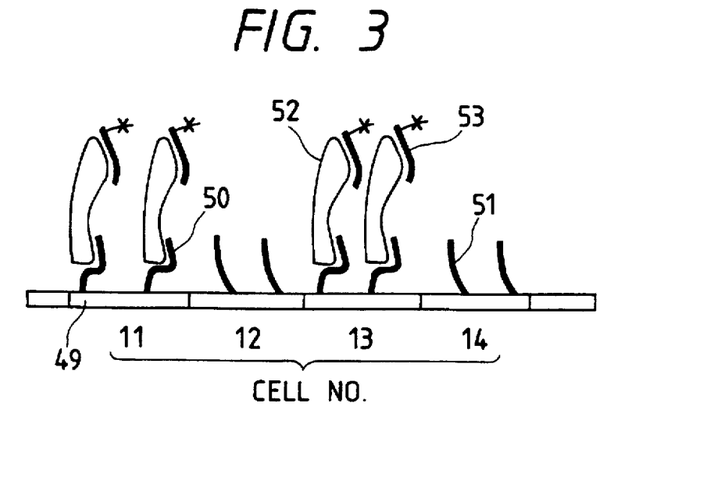
FIG. 3 is a schematic view depicting the state when reaction is completed in the reaction chip.
Figure 4:
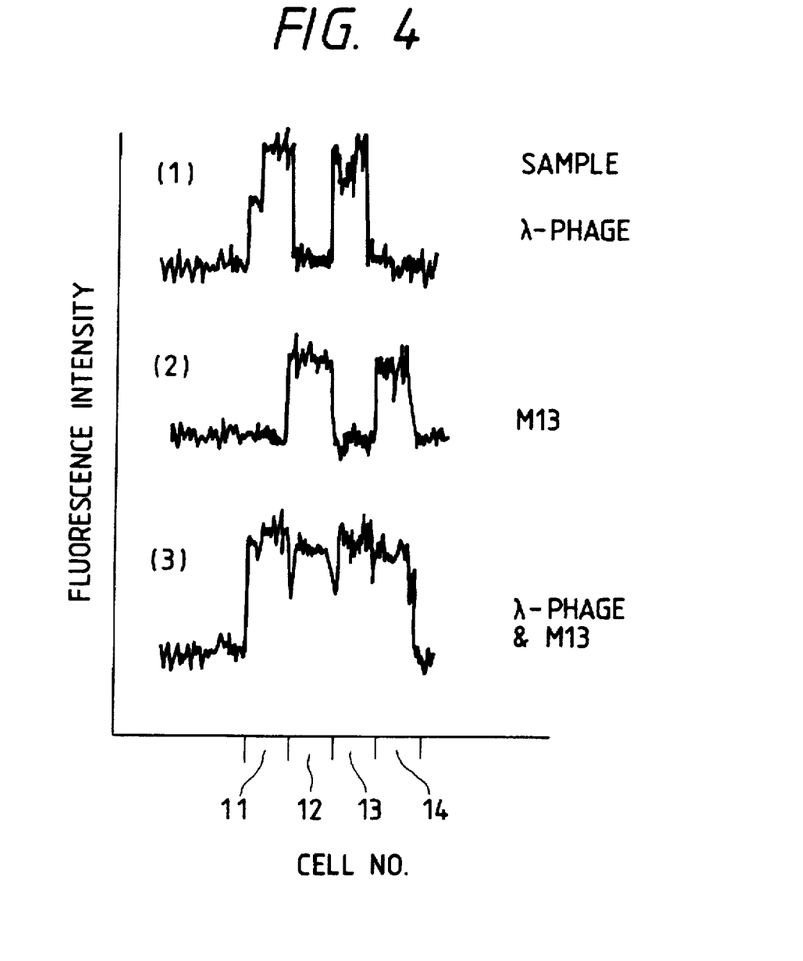
FIG. 4 is a view depicting the results of fluorescence measurement.

FIG. 3 depicts the state wherein a target polynucleotide, λ-phage DNA is bonded to the labeled probe. As a second example of the immobilized probe chip, herein, there was employed the one produced by immobilizing the first probe for λ phage and a third probe for M13 phage following the procedure described above. To the cells Nos. 11 and 13 on the surface of chip 49 is bonded probe 50 for λ-phage DNA while probe 51 for M13 phage is bonded to the cells Nos. 12 and 14. The denatured λ phage 52 as a target is bonded to the λ-phage probe on the cells 11 and 13, but is not bonded to the M13 phage probe on the cells 12 and 14. To the λ phage captured on the cells is bonded fluorescent dye-labeled probe 53. FIG. 4 depicts the results of actually measuring a sample containing λ phage alone, a sample containing M13 phage alone and a sample containing the two individually. As is shown in FIG. 4 (1), fluorescence is detected on the cells 11 and 13, with the immobilized λ-phage probe. As is shown in FIG. 4 (2), fluorescence is detected on the cells 12 and 14, with the immobilized M13 phage probe. As is shown in FIG. 4 (3), fluorescence is detected on all of the cells with the immobilized λ-phage probe and with the immobilized M13 phage probe. As has been described above, the presence or absence of a target polynucleotide can be determined on the basis of the portion where fluorescence is detected.

As has been described above, the present invention is used for detecting a plurality of target polynucleotides on a single reaction chip. Thus, the present invention proposes an advantage in that only a single reaction procedure is needed for carrying out a plurality of tests. In case of screening viruses or the like, in particular, subjects for measurement are unknown, generally, so that all potential testing items therefor are preferably tested. The present invention also provides an advantage in that a greater number of items can be measured at a less amount of a sample, compared with conventional tests. This proposes an advantage in that human subjects are exposed to less burdens in collecting body fluids and tissues as measuring subjects.

As is shown in the second example of the chip described above, the immobilization of a single capturing probe onto a plurality of cells and the use thereof can increase detection precision compared with the case when probes are immobilized on a single cell. Furthermore, as is shown in the former part of the present Example described above, the immobilization and use of a plurality of probes onto different cells for a single analytical subject enables the detection of a single polynucleotide using a plurality of different polynucleotide capturing probes, which thus proposes an advantage in that detection precision can be raised compared with the conventional detection method using a probe of a single species. That is, in the first example of the chip of the present Example described above, it is determined as follows; if fluorescence is detected in the first and second cells, λ phage is contained in a sample; if fluorescence is detected only in either cell, a sample may contain λ phage which is suspicious; if no fluorescence is detected in any of the cells, the amount of λ phage in a sample may be quite less. According to the conventional method using a capturing probe of a single species, a contaminating substance similar to a target polynucleotide, if any in a sample, may eventually be detected by mistake, whereas in accordance with the present invention, a plurality of capturing probes immobilized onto different regions are used for detection, giving an advantage in that the influence of such contaminating substance may be decreased.

According to the conventional method, nylon and nitrocellulose membranes are used as supports, which causes inconvenience for handling because of their less mechanical strength. The present invention is suitable for automatic analysis because chips of silicon and the like are used therein.

EXAMPLE 2

Explanation will now follow concerning a method for efficiently effecting the screening of probes for use in DNA diagnostics, employing the present invention.

If the sequence of a target polynucleotide is unknown, the probes for known sequences cannot be used. According to the conventional method, it has been required to determine a part or the whole of the sequence of a target polynucleotide. A method will now be explained, comprising screening probes using the present invention without directly determining the target polynucleotide sequence.

The polynucleotide probes to be used in the present invention individually contain 3' terminal CAT and a 12-bp oligonucleotide composed of a random 3-bp combination of XAA, XGA, XTA, XCA, XAG, XGG, XTG, XCG, XAT, XGT, XTT, XCT, XAC, XGC, XTC, and XCC, and to 5' terminus thereof is bonded an amino group through a spacer. Therefore, the polynucleotide probes to be used in the present Example are in total 4096 types. Herein, X represents the spacer, and as such, there is employed a substance which does not specifically bond individual bases. Following the procedure of Example 1, each probe is immobilized onto each cell on a reaction chip. As sample models, those with Sequence Nos. 10 and 11 are fluorescence labeled by the following method for use. Firstly, a T4 polymerase kinase is used to introduce a phosphate group into the 5' terminus of the sample polynucleotide, according to the method of L. E. Morrison et al. described in Analytical Biochemistry 183, 231–244(1989).

Then, the reaction in a solution, pH 6 containing 0.2M 1-ethyl-3-(dimethylaminopropyl)carbodiimide carbodiimide and 0.5M ethylenediamine is effected for 18 hours to introduce the amino group into the 5' terminus. After repetition of the ethanol precipitation for removal of unreacted ethylenediamine, there follows the reaction with sulforhodamine 101 acid chloride suspension of a final concentration of 20 mM (60 to 100-fold molar volume of target oligonucleotide) in 0.1M carbonate buffer, pH 9 containing 20% acetonitrile. Removing the unreacted sulforhodamine 101 acid chloride with ethanol precipitation, produces a polynucleotide sample with the 5' terminus labeled with sulforhodamine 101. The polynucleotide sample labeled with sulforhodamine 101 reacts with the chip with the 4096 types of probes immobilized onto each cell under hybridization conditions, following Example 1. The non-specifically adsorbed part of the polynucleotide sample is removed with a washing solution at 55° C.

Following Example 1, the fluorescence emitted from each cell of the reaction chip is measured by using He/Ne laser (594 nm) (or Na lamp or the like) and a photomultiplier (or a high-sensitivity line sensor and area sensor). A combination of other light sources and fluorophores may be used satisfactorily. Consequently, it is observed that the polynucleotide sample of Sequence No. 10 is bonded to the cell with the following five types of oligonucleotides immobilized;

5' XTTXTTXGTCAT 3' Seq. ID No:1

5' XTAXCAXAGCAT 3' Seq. ID. No:2

5' XAAXCAXAACAT 3' Seq. ID. No:3

5' XACXGAXTACAT 3' Seq. ID. No:4

5' XAGXTTXTGCAT 3' Seq. ID. No:5

It is observed that the polynucleotide sample of Sequence No. 11 is bonded to the cell with the following two types of oligonucleotides immobilized;

5' XCAXCAXGGCAT 3' Seq. ID. No:6

5' XTCXGAXACCAT 3' Seq. ID. No:7

As has been described above, different polynucleotides are to be bonded to different cells on a chip in accordance with the present invention. Because the cell with the immobilized probes to be used in the present invention encompasses all of the possible sequences of a target polynucleotide region starting ATG and having 11 base pairs, it is advantageous that a probe of an oligonucleotide of an unknown sequence can be screened. Because the target polynucleotide region starting ATG may correspond to a DNA open reading frame, a, such probe having ATG is useful for screening a polynucleotide fragment possibly containing an open reading frame.

EXAMPLE 3

Other examples of the present invention will now be explained hereinbelow.

The polynucleotides to be used in the present Example are as follows:

polynucleotide having a nucleotide sequence, Sequence No. 1; Probe No. 1;

polynucleotide having a nucleotide sequence, Sequence No. 2; Probe No. 2;

polynucleotide having a nucleotide sequence, Sequence No. 7; Probe No. 3;

polynucleotide having a nucleotide sequence, Sequence No. 8; Probe No. 4;

polynucleotide having a nucleotide sequence, Sequence No. 9; Probe No. 5.

In the present Example, explanation will follow regarding a method for separating a λ-phage DNA decomposition product as a target polynucleotide sample.

Figure 5:
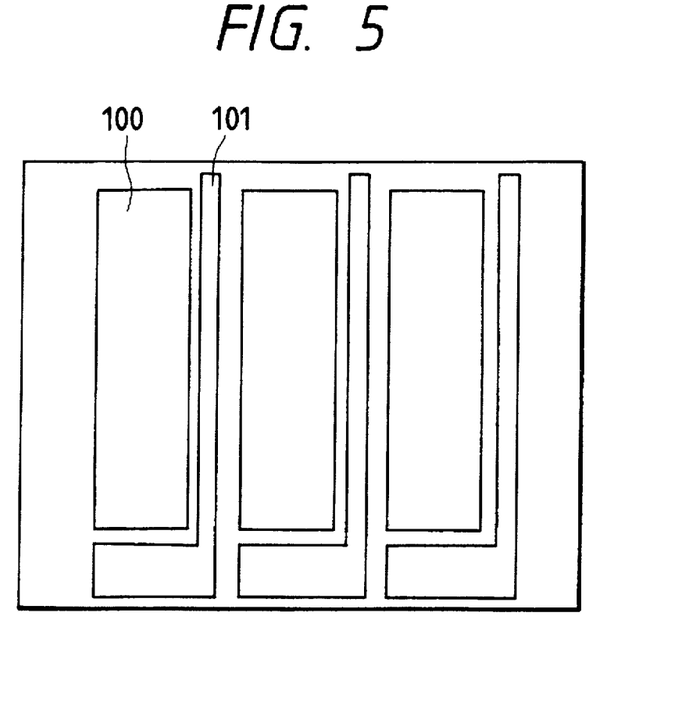
FIG. 5 is an enlarged plan view schematically depicting the reaction part in accordance with the present invention.

The first to fifth probes are capturing probes recognizing different sites of λ-phage DNA as the target polynucleotide. These are immobilized onto the reaction parts of the reaction chip according to the method of Example 1. As is shown in FIG. 5 depicting the enlarged reaction parts, the cells of the reaction chip to be used herein function also as target polynucleotide separation electrodes 100. Counter electrodes 101 are arranged between the individual cells. FIG. 6 generally depicts the view of the recovery method of target polynucleotide. On substrate 90 are formed target polynucleotide capturing electrodes 111, 113, 115, 117, 119 and counter electrodes 112, 114, 116, 118, 120. In the present Example, the Hind III fragments of λ-phage DNA are added on sample addition part 93 of the support with five types of immobilized probes for capturing DNA, under hybridization conditions. After washing off unreacted substances, the washing solution is then discharged from unreacted solution removing part 94. The procedures thus described are carried out following Example 1. By the procedures, five fragments are captured among the six Hind III fragments. While applying an electric field so as to maintain each cell as positive electrode and the counter electrodes as negative electrodes, a separation solution containing 2.4M tetraethylammonium chloride is added from the sample addition part 93 for heating to 65° C. to 70° C. The separation solution then covers the reaction container in its entirety as shown by 92, and an electric field is applied so as to prepare cells with electrodes for dissociation of hybridized polynucleotides 111, 113,115, 117,119 as positive electrodes and counter electrodes 112, 114,116,118, 120 as negative electrodes. The target polynucleotides are not eluted at this point because of their negative charge. Then, capillary 131 provided with electrode 132 for capturing eluted target polynucleotides is placed in cell 119, followed by application of an electric field so as to prepare the cell 119 as negative electrode and the electrode 132 in the capillary as positive charge. By the procedure, a first target polynucleotide is recovered and separated. The same procedure is repeated for cells 117,115, 113, 111 in this order, to recover five types of target polynucleotides. The recovered target polynucleotides are subjected to the analysis with polyacrylamide electrophoresis. It is suggested that the solutions recovered from the cells 119,117, 115, 113, 111 contain polynucleotides of about 2,000 bp, about 6,600 bp, about 2,300 bp, about 130 bp and about 9,400 bp.

As has been described above, a plurality of target polynucleotides can be separated and recovered readily using the present invention.

As has been described above, also, the present invention enables the simultaneous detection of a plurality of target polynucleotides with a single reaction chip, so it is advantageous to require less reaction procedures compared with the conventional method requiring one to prepare one reaction chip per target polynucleotide. Also, the volume of a sample solution should be less because the solution is used for only a single reaction procedure. Furthermore, by detecting a single target polynucleotide with a plurality of probes, the reliability of the measuring results gets higher than the reliability of the conventional methods. According to the present method, a plurality of target polynucleotides can be separated advantageously.

Sequence Table

Sequence No. 1
  Sequence length: 27
  Sequence type: nucleic acid
  Number of chains: single strand
  Topology: linear
  Sequence species: synthetic polynucleotide
  Sequence:
  5' CAGAAGAGTT AGTTGACTAT ACAGCCA 3' Seq. ID. No:8

Sequence No. 2
  Sequence length: 27
  Sequence type: nucleic acid
  Number of chains: single strand
  Topology: linear
  Sequence species: synthetic polynucleotide
  Sequence:
  5' ATGTTCAGGC AGGGATGTTC TCACCTA 3' Seq. ID. No:9

Sequence No. 3
  Sequence length: 27
  Sequence type: nucleic acid
  Number of chains: single strand
  Topology: linear
  Sequence species: synthetic polynucleotide
  Sequence:
  5' ATATAATCCT GATTGTTTGG ATTATAC 3' Seq. ID. No:10

Sequence No. 4
  Sequence length: 27
  Sequence type: nucleic acid
  Number of chains: single strand
  Topology: linear
  Sequence species: synthetic polynucleotide
  Sequence:
  5' AAACTAGCAT GTCAATCATA TGTACCC 3' Seq. ID. No:11

Sequence No. 5
  Sequence length: 40
  Sequence type: nucleic acid
  Number of chains: single strand
  Topology: linear
  Sequence species: synthetic polynucleotide Sequence:
5' GAGGTGGATA TGGGCCGCAG TGAGGAGAAT
AACATCACGC 3' Seq. ID. No:12

Sequence No. 6
Sequence length: 40
Sequence type: nucleic acid
Number of chains: single strand
Topology: linear
Sequence species: synthetic polynucleotide
Sequence:
5' TAAGTATAGC CCGGAATAGG TGTATCACCG
TACTCAGGAG 3' Seq. ID. No:13

Sequence No. 7
Sequence length: 27
Sequence type: nucleic acid
Number of chains: single strand
Topology: linear
Sequence species: synthetic polynucleotide
Sequence:
5' CCTACAACCT TAGTAGTTGG TAACCTG 3' Seq. ID. No:14

Sequence No. 8
Sequence length: 27
Sequence type: nucleic acid
Number of chains: single strand
Topology: linear
Sequence species: synthetic polynucleotide
Sequence:
5' ATGACCGCAC CAACAGGCTC CAAGCCA 3' Seq. ID. No:15

Sequence No. 9
Sequence length: 27
Sequence type: nucleic acid
Number of chains: single strand
Topology: linear
Sequence species: synthetic polynucleotide
Sequence:
5' AGCACAAAGC CTCGCAATCC AGTGCAA 3' Seq. ID. No:16

Sequence No. 10
Sequence length: 200
Sequence type: nucleic acid
Number of chains: single strand
Topology: linear
Sequence species: synthetic polynucleotide
Sequence:
5' AGCTTTGCAC TGGATTGCGA GGCTTTGTGC
TTCTCTGGAG TGCGACAGGT TTGATGACAA
AAAATTAGCG CAAGAAGACA AAAATCACCT
TGCGCTAATG CTCTGTTACA GGTCACTAAT
ACCATCTAAG TAGTTGATTC ATAGTGACTG
CATATGTTGT GTTTTACAGT ATTATGTAGT
CTGTTTTTTA TGCAAAATCT 3' Seq. ID. No:17

Sequence No. 11
Sequence length: 201
Sequence type: nucleic acid
Number of chains: single strand
Topology: linear
Sequence species: synthetic polynucleotide
Sequence:
5' AATTTAATAT ATTGATATTT ATATCATTTT
ACGTTTCTCG TTCAGCTTTT TTATACTAAG
TTGGCATTAT AAAAAAGCAT TGCTTATCAA
TTTGTTGCAA CGAACAGGTC ACTATCAGTC
AAAATAAAAT CATTATTTGA TTTCAATTTT
GTCCCACTCC CTGCCTCTGT CATCACGATA
CTGTGATGCC ATGGTGTCCG A 3' Seq. ID. No:18

---

What is claimed is:

1. A polynucleotide separating device for capturing, eluting and collecting a plurality of target polynucleotides in a sample solution comprising;

a plurality of cells for immobilizing individually different probes complementary to a plurality of target polynucleotides, each cell being formed at a different region on a single polynucleotide capturing support, wherein said target polynucleotides hybridize with said probes, and wherein a surface of each cell has an electrode for supplying an electric field to each cell separately to elute the hybridized target polynucleotides from said cell individually and a single capillary for collecting the eluted target polynucleotides from each of said cells, wherein said capillary has another electrode and is movable into a position above each of said cells.

2. A polynucleotide separating device according to claim 1, wherein said plurality of cells are formed at different regions on a single chip.

3. A polynucleotide separating device according to claim 12, further comprising a protective film on said single chip at locations other than said plurality of cells on said single chip.

4. A polynucleotide separating device according to claim 1, further comprising means for detecting said eluted target polynucleotides collected by said single capillary.

5. A polynucleotide separating device according to claim 1, further comprising means for switching an electric field applied to at least one of the electrodes thereby effecting the elution and separation of a plurality of the target polynucleotides.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:1:

T T T T G T C A T                                                                                           9

( 2 ) INFORMATION FOR SEQ ID NO:2:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:2:

TACAAGCAT 9

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:3:

AACAAACAT 9

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:4:

ACGATACAT 9

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:5:

AGATTTGCAT 10

( 2 ) INFORMATION FOR SEQ ID NO:6:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO (x i) SEQUENCE DESCRIPTION: SEQ ID NO:6:

CACAGGCAT                                                                                                         9

(2) INFORMATION FOR SEQ ID NO:7:

(i) SEQUENCE CHARACTERISTICS:
        (A) LENGTH: 9 base pairs
        (B) TYPE: nucleic acid
        (C) STRANDEDNESS: single
        (D) TOPOLOGY: linear     (i i) MOLECULE TYPE: DNA (genomic)

(i i i) HYPOTHETICAL: YES

(i v) ANTI-SENSE: NO

(x i) SEQUENCE DESCRIPTION: SEQ ID NO:7:

TCGAACCAT                                                                                                         9

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (i i) MOLECULE TYPE: DNA (genomic)

(i i i) HYPOTHETICAL: YES

(i v) ANTI-SENSE: NO

(x i) SEQUENCE DESCRIPTION: SEQ ID NO:8:

CAGAAGAGTT AGTTGACTAT ACAGCCA                                                                                    27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (i i) MOLECULE TYPE: DNA (genomic)

(i i i) HYPOTHETICAL: YES

(i v) ANTI-SENSE: NO

(x i) SEQUENCE DESCRIPTION: SEQ ID NO:9:

ATGTTCAGGC AGGGATGTTC TCACCTA                                                                                    27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (i i) MOLECULE TYPE: DNA (genomic)

(i i i) HYPOTHETICAL: YES

(i v) ANTI-SENSE: NO

(x i) SEQUENCE DESCRIPTION: SEQ ID NO:10:

ATATAATCCT GATTGTTTGG ATTATAC                                                                                    27

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:11:

AAACTAGCAT GTCAATCATA TGTACCC    27

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:12:

GAGGTGGATA TGGGCCGCAG TGAGGAGAAT AACATCACGC    40

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:13:

TAAGTATAGC CCGGAATAGG TGTATCACCG TACTCAGGAG    40

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: YES

( i v ) ANTI-SENSE: NO

( x i ) SEQUENCE DESCRIPTION: SEQ ID NO:14:

CCTACAACCT TAGTAGTTGG TAACCTG    27

( 2 ) INFORMATION FOR SEQ ID NO:15:

( i ) SEQUENCE CHARACTERISTICS:

(A) LENGTH: 27 base pairs
(B) TYPE: nucleic acid
(C) STRANDEDNESS: single
(D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:15:

ATGACCGCAC CAACAGGCTC CAAGCCA                                              27

(2) INFORMATION FOR SEQ ID NO:16:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:16:

AGCACAAAGC CTCGCAATCC AGTGCAA                                              27

(2) INFORMATION FOR SEQ ID NO:17:

(i) SEQUENCE CHARACTERISTICS:
    (A) LENGTH: 200 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:17:

AGCTTTGCAC TGGATTGCGA GGCTTTGTGC TTCTCTGGAG TGCGACAGGT TTGATGACAA           60

AAAATTAGCG CAAGAAGACA AAAATCACCT TGCGCTAATG CTCTGTTACA GGTCACTAAT          120

ACCATCTAAG TAGTTGATTC ATAGTGACTG CATCTGTTGT GTTTACAGT ATTATGTAGT           180

CTGTTTTTTA TGCAAAATCT                                                      200

(2) INFORMATION FOR SEQ ID NO:18:

(i) SEQUENCE CHARACTERISTICS:
    (A) LENGTH: 201 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:18:

AATTTAATAT ATTGATATTT ATATCATTTT ACGTTTCTCG TTCAGCTTTT TTATACTAAG           60

TTGGCATTAT AAAAAAGCAT TGCTTATCAA TTTGTTGCAA CGAACAGGTC ACTATCAGTC          120

```
AAAATAAAAT  CATTATTTGA  TTTCAATTTT  GTCCCACTCC  CTGCCTCTGT  CATCACGATA      180

CTGTGATGCC  ATGGTGTCCG  A                                                   201
```